United States Patent [19]
Gallant et al.

[11] Patent Number: 5,966,760
[45] Date of Patent: Oct. 19, 1999

[54] APPARATUS AND METHOD FOR UPGRADING A HOSPITAL ROOM

[75] Inventors: Dennis J. Gallant, Harrison, Ohio; John W. Ruehl, Shelbyville, Ind.; John C. Gray, Great Falls, Mont.; Edward W. Catton, New Palestine, Ind.

[73] Assignee: Hill-Rom, Inc., Batesville, Ind.

[21] Appl. No.: 08/792,881

[22] Filed: Jan. 31, 1997

[51] Int. Cl.⁶ .................................................. A47C 21/00
[52] U.S. Cl. .................................. 5/658; 5/510; 5/507.1; 5/503.1
[58] Field of Search ........................ 5/510, 503.1, 507.1, 5/658; 248/292.12, 404, 410, 414; 137/597, 884, 557; 29/157, 428

[56] References Cited

U.S. PATENT DOCUMENTS

| | | | |
|---|---|---|---|
| 3,026,079 | 4/1962 | Stack ................................... | 248/292.12 |
| 4,494,572 | 1/1985 | Loveless ............................. | 137/596.17 |
| 4,547,092 | 10/1985 | Vetter et al. .................................. | 5/658 |
| 4,646,211 | 2/1987 | Gallant et al. . | |
| 4,672,728 | 6/1987 | Nimberger ................................ | 29/157 |
| 4,821,470 | 4/1989 | Kappers et al. . | |
| 5,060,425 | 10/1991 | Kappers et al. . | |
| 5,072,906 | 12/1991 | Foster . | |
| 5,117,521 | 6/1992 | Foster et al. . | |
| 5,186,337 | 2/1993 | Foster et al. . | |
| 5,284,255 | 2/1994 | Foster et al. . | |
| 5,299,773 | 4/1994 | Bertrand ............................. | 248/292.12 |
| 5,323,565 | 6/1994 | Kappers et al. . | |
| 5,335,651 | 8/1994 | Foster et al. . | |
| 5,337,845 | 8/1994 | Foster et al. . | |
| 5,370,111 | 12/1994 | Reeder et al. . | |
| 5,377,371 | 1/1995 | Foster . | |
| 5,398,359 | 3/1995 | Foster . | |
| 5,457,831 | 10/1995 | Foster et al. . | |
| 5,562,091 | 10/1996 | Foster et al. . | |
| 5,567,885 | 10/1996 | Garside ............................... | 73/861.07 |
| 5,602,345 | 2/1997 | Wenger et al. .................... | 73/861.357 |
| 5,681,116 | 10/1997 | Lin ...................................... | 248/298.1 |
| 5,720,317 | 2/1998 | Nimberger .............................. | 137/597 |
| 5,725,024 | 3/1998 | Nimberger .............................. | 137/597 |

OTHER PUBLICATIONS

"Lettuce Trade Your Spaghetti For The CABG Cart", CABG Cart advertising brochure, 5 pages, date unknown.

"Stabilet From Hill–Rom", Hill–Rom product brohure, 6 pages, 1992.

*Primary Examiner*—Michael F. Trettel
*Assistant Examiner*—Fredrick Conley
*Attorney, Agent, or Firm*—Barnes & Thornburg

[57] ABSTRACT

An apparatus is provided to permit upgrading of a hospital room from a general care room to a critical care room and to facilitate transport of a critical care patient on a hospital bed.

37 Claims, 7 Drawing Sheets

APPARATUS AND METHOD FOR UPGRADING A HOSPITAL ROOM

BACKGROUND AND SUMMARY OF THE INVENTION

The present invention relates to an apparatus and method to facilitate upgrading of a standard, general care hospital room to a critical room. More particularly, the present invention relates to an improved apparatus and method for providing seamless critical care services to a patient in a hospital room and during transport of the patient within the hospital.

Recent trends have caused cost reducing pressures on hospitals. These cost pressures have driven traditional in-patient services to less expensive out-patient and home care settings. Therefore, hospitals tend to have smaller in-patient populations. Future in-patient populations are likely to be older and sicker patients with multiple complications. The population of intermediate care patients is also likely to increase while the med-surg hospital population is decreasing over time. Therefore, the in-patient hospital population has a higher level of acuity.

Hospitals will likely have fewer beds in the future. Reconstruction of hospital rooms for critical care services is very expensive. Typically, existing structures must be torn out and rebuilt with critical care capabilities.

It is known to provide a pivoting power column built within the room to provide life support services for critical care patients. These pivoting power columns, however, are not transportable and must be built within the particular hospital room. See, for example, U.S. Pat. No. 5,398,359; U.S. Pat. No. 5,377,371; U.S. Pat. No. 5,284,255; U.S. Pat. No. 5,186,337; and U.S. Pat. No. 5,072,906.

Several problems face hospital administrators and planners. Facilities within inflexible architectural systems restrict the ability of institutions to upgrade services quickly and inexpensively. In addition, the process of transporting critical care patients creates adverse conditions and risks for staff and patients due to the inability to easily move and maintain power for the ventilator and/or IV pumps and transport monitor.

In order to adapt to changes for fewer but more acute patients, hospitals need the option for more responsive architectural systems and patient rooms that can be upgraded to critical care or downgraded to med-surg quickly and inexpensively. In order to accomplish these needs and to reduce the number of staff and time required to transport a critical care patient, hospitals need a mobile equipment system that can support and provide power, medical gases, and a communication interface to a ventilator, IV pumps and/or a patient monitor. The system must consume minimum space within a patient room, be able to fit substantially within the footprint of the patient bed during transport, and organize and manage lines connected to the patient.

The apparatus and method of the present invention provides both an architectural headwall and a portion of the headwall that is mobile to allow a hospital to create a "general care" patient room that can be upgraded quickly and efficiently to a critical care room "upon demand" without remodeling the room. The apparatus of the present invention includes a general care "flexible" headwall with services that can be upgraded or downgraded easily. In addition, a care cart is provided that supports critical care devices such as the ventilator, pumps, etc. at the bedside. The care cart can be coupled to the patient bed for manually transporting the patient. During the transport the mobile care cart provides uninterrupted power for critical care devices.

The apparatus and method of the present invention provides several transport benefits. The apparatus reduces the time for preparing for transport and reduces the time required for disconnecting and handling of equipment. In addition, fewer staff are required for transport. The battery supply maintains uninterrupted power during transport as well as uninterrupted oxygen and air supply for ventilator patients. In the room, the apparatus and method of the present invention provides the flexibility to reposition services around the bed. Therefore, the present invention provides improved patient head access. The mobile care cart can also nest with the headwall to provide a compact design.

The apparatus and method of the present invention provides an improved headwall design for supporting med-surg patients. The headwall design provides minimal services including oxygen, air, vacuum, nurse call, and electricals. When it is desired to upgrade a room to a critical care room, a mobile care cart module of the present invention is transported into the room. The mobile care cart provides a means for efficiently upgrading a patient room to provide critical care services while minimizing construction and down time. The mobile care cart includes provisions for suction, oxygen, air, electrical outlets, and a battery power supply. A power assist drive mechanism can be included on the care cart, if desired.

The system of the present invention therefore provides basic universal services on the headwall. The hospital room can be upgraded to critical care "on demand" or just-in-time.

The headwall of the present invention includes an improved concealment cover to provide an aesthetically pleasing appearance. The concealment cover acts as a folding top surface. The foldable concealment cover can be folded within a raceway of the headwall to provide access to a track for hanging accessory items from the top of the raceway of the headwall.

The care cart provides a platform for mounting primary critical care equipment. A ventilator is mounted on a movable, power assisted and adjustable shelf so that the ventilator can be positioned in an elevated position when the mobile care cart is used in the hospital room. The care cart can also be provided with a fixed shelf or multiple fixed shelves, if desired. When it is desired to transport the critically ill patient within the hospital, the mobile care cart is disconnected from the headwall and connected to an end of the patient's hospital bed. An onboard power supply on the care cart supports the ventilator during transport. Manifolds are provided on the care cart for holding oxygen and air tanks which are connected to the ventilator during transport. Pivoting IV poles on the care cart can swing into a nested position adjacent the bed for transport. During transport, the equipment shelf is lowered to a position below the bed. The equipment shelf may be rotated so that the caregiver can view the equipment control panel during transport.

The care cart of the present invention is designed to provide seamless care for the patient. In other words, the caregiver does not have to rehandle or disconnect equipment that is connected to the patient to transport the patient.

The apparatus and method of the present invention may reduce the number of staff required to transport a critically ill patient. Typically, up to five people are required to transport the patient. With the apparatus and method of the present invention, two people can transport the patient.

While the critical care patient remains in the hospital room, the mobile care cart integrates with and is nested with the headwall. The care cart is connected to the main power supply of the room and the ventilator is connected to oxygen or air supplies in the headwall in a conventional manner.

According to one aspect of the present invention, an apparatus is provided to permit upgrading of a hospital room from a general care room to a critical care room and to facilitate transport of a critical care patient on a hospital bed or stretcher. The apparatus includes a headwall mounted to a wall of the hospital room. The headwall includes electrical outlets, gas supply outlets, and a bed locator section. The apparatus also includes a mobile care cart including a base having a plurality of casters, fixed or motorized adjustable equipment shelf coupled to the base, equipment located on the equipment shelf, a gas manifold, a medical gas supply line for coupling the gas manifold to a gas outlet of the headwall when the care cart is in the hospital room, and means for coupling the manifold to a transportable gas supply mounted on the mobile care cart during transport. The apparatus further includes a battery coupled to the base, and a power cord configured to be plugged into the electrical outlet in the headwall for recharging the battery and for powering the critical care unit when the mobile care cart is in the hospital room. The battery provides an uninterrupted power supply to select critical equipment when the power cord is unplugged for transport.

The mobile care cart is configured to be moved into the hospital room and located adjacent the patient hospital bed and the bed locator section of the headwall to upgrade the hospital room to a critical care room. The care cart also includes a latching mechanism for coupling the care cart to the hospital bed to provide a secure, stable connection during transport.

According to another aspect of the present invention, a mobile care cart includes a base including a plurality of casters, a latching mechanism on the base that can be adjusted for various types of hospital beds and equipment, a movable support coupled to the base, a drive mechanism coupled to the base and to the support to move the movable support from an elevated position to a downwardly extended, transport position, and an equipment shelf rotatably coupled to the movable support. The equipment shelf is rotatable relative to the base to facilitate access to an item of equipment located on the equipment shelf.

In the illustrated embodiment, the equipment shelf is located under an end of the hospital bed when the base is coupled to the hospital bed and the movable support is in its transport position. The equipment shelf is slidably coupled to the movable support to permit lateral movement of the equipment shelf relative to the support and the base in a direction normal to an axis of rotation of the equipment shelf.

Also in the illustrated embodiment, the apparatus includes electrical outlets coupled to the base for powering the items of equipment, a battery coupled to the base, and a power cord configured to be plugged into the electrical outlet in the headwall for recharging the battery and for powering the item of equipment when the mobile care cart is in the hospital room. The battery provides an uninterrupted power supply to the item of equipment when the power cord is unplugged for transport.

The illustrated embodiment further includes an indicator coupled to said base for indicating the condition of the battery. The indicator includes a display panel on the mobile care cart and an alarm coupled to the cart for providing an audible signal indicative of the condition of the battery.

According to yet another aspect of the present invention, a mobile care cart includes a latch mechanism for coupling the cart to a hospital bed during transport of the bed. The care cart also includes an on-board battery and gas supply for supplying electrical and gas outlets, respectively, on the care cart for use by equipment during transport. The care cart is nestable against a headwall when in the hospital room. The care cart further includes means for coupling the electrical and gas supply outlets on the care cart to electrical and gas supplies separate from the care cart when the care cart is in a hospital room. The coupling means automatically switches to use of the on-board battery and gas supply to provide an uninterrupted gas and electrical supply during transport when the cart is disconnected from the electrical and gas supplies separate from the care cart for transport.

According to a further aspect of the present invention, a mobile care cart apparatus includes a movable base, and a manifold assembly coupled to the base. The manifold assembly includes a manifold block having a gas inlet configured to be coupled to a gas tank located on the mobile care cart and a gas outlet. The apparatus also includes a cross over valve having a first input coupled to the gas outlet of the manifold, a second input configured to be coupled to a wall outlet gas supply by a gas supply hose, and an outlet. The outlet of the cross over valve is configured to be coupled to an item of equipment located on the care cart by a gas supply line. The cross over valve is configured to supply gas to the cross over valve outlet from the gas tank automatically when the wall outlet gas supply is disconnected from the gas supply hose and to supply gas to the crossover valve outlet from the wall outlet gas supply when the wall outlet gas supply is connected to the gas supply hose.

The illustrated manifold block includes first and second gas inlets coupled to the gas outlet. The first and second inlets are configured to be coupled to first and second gas tanks, respectively, for supplying gas to the outlet of the manifold from both of the first and second gas tanks. The illustrated manifold block also includes first and second recessed portions configured to receive a valve stem of the first and second gas tanks, respectively, and first and second latching brackets for securing the first and second gas tanks to the manifold block so that the manifold block protects the valve stems of the first and second gas tanks. The apparatus further includes first and second pressure gauges coupled to the first and second inlets to provide an indication of the pressure within the first and second tanks, respectively.

According to a still further aspect of the present invention, a mobile care cart apparatus is configured to be located adjacent a hospital bed during transport of the hospital bed. The mobile care cart apparatus includes a movable base, and a manifold assembly coupled to the base. The manifold assembly includes a manifold block having a gas inlet configured to be coupled to a gas tank located on the mobile care cart and a gas outlet configured to be coupled to an item of equipment located on the care cart by a gas supply line. The apparatus also includes a spring-loaded platform coupled to the base. The spring-loaded platform is configured to support a gas tank on the base to facilitate adjustment of the tank relative to the manifold.

According to another aspect of the present invention, a mobile care cart apparatus is configured to be located adjacent a hospital bed during transport of the hospital bed. The mobile care cart apparatus includes a movable base, and a manifold assembly coupled to the base. The manifold assembly includes a manifold block having a gas inlet configured to be coupled to a gas tank located on the mobile care cart and a gas outlet configured to be coupled to a first item of equipment located on the care cart by a gas supply line. The apparatus also includes an auxiliary gas flow control valve coupled to the outlet of the manifold for providing auxiliary gas flow to a second item of equipment on the care cart.

According to yet another aspect of the present invention, a mobile care cart apparatus is configured to be located adjacent a hospital bed during transport of the hospital bed. The mobile care cart apparatus includes a movable base, a power supply on the base, and a vacuum pump located on the base of the care cart and coupled to the power supply to provide suction on the care cart during transport.

According to an additional aspect of the present invention, a pressure regulator apparatus is provided for reducing pressure of a gas received from a gas outlet aperture formed in a planar surface and for delivering reduced pressure gas to a gas inlet aperture formed in the planar surface spaced apart from the gas outlet aperture by a first distance. The regulator apparatus includes a regulator body for reducing gas pressure. The body includes an end wall having a regulator inlet configured to be coupled to the gas outlet aperture, a first annular seal located a second distance from the regulator inlet, a second annular seal located a third distance from the regulator inlet, and a regulator outlet formed in the end wall between the first and second seals. The second distance is less than the first distance, and the third distance is greater than the first distance. The first and second seals are configured to engage the planar surface on opposite sides of the gas inlet aperture so that gas from the regulator outlet flows into the gas inlet aperture formed in the planar surface.

In the illustrated apparatus, the end wall is formed to include an annular groove surrounding the regulator inlet. The annular groove is spaced apart from the regulator inlet by the first distance so that the annular groove is aligned with the gas inlet aperture formed in the planar surface when the regulator inlet is coupled to the gas outlet aperture. The regulator outlet is formed in communication with the annular groove.

Also in the illustrated apparatus, the regulator inlet includes a threaded stem configured to be coupled to the gas outlet aperture. The first and second seals are O-ring seals located within first and second annular notches formed in the end wall of the regulator body.

Additional objects, features, and advantages of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
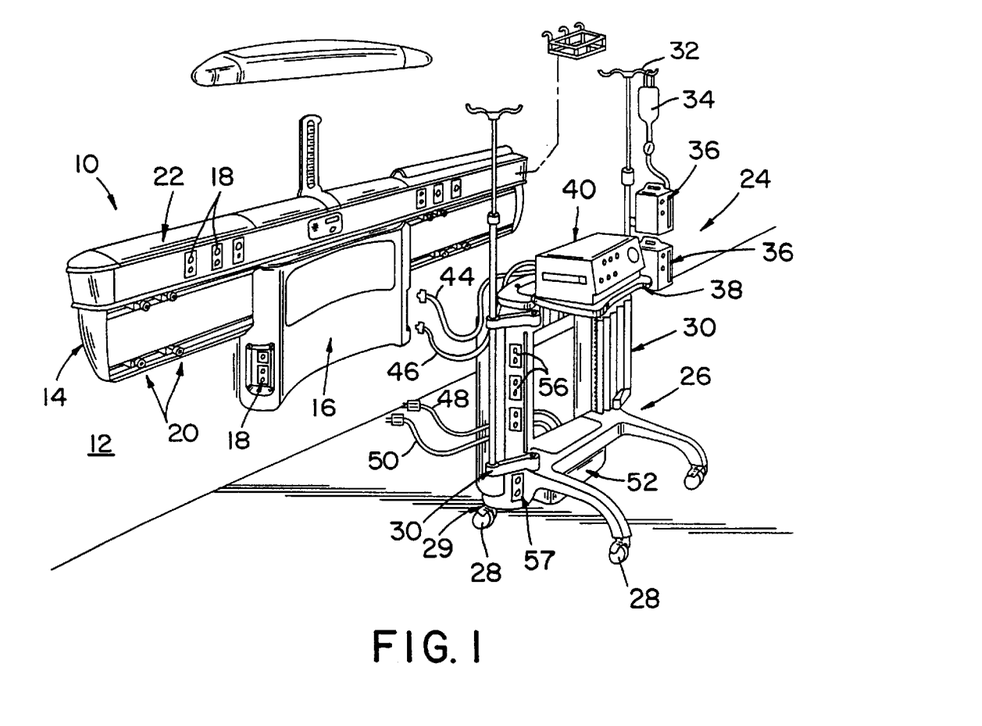
FIG. 1 is a perspective view of the system of the present invention including a headwall mounted on a hospital room wall and a mobile care cart configured to be located adjacent the headwall to upgrade the hospital room to a critical care room.
Figure 2:
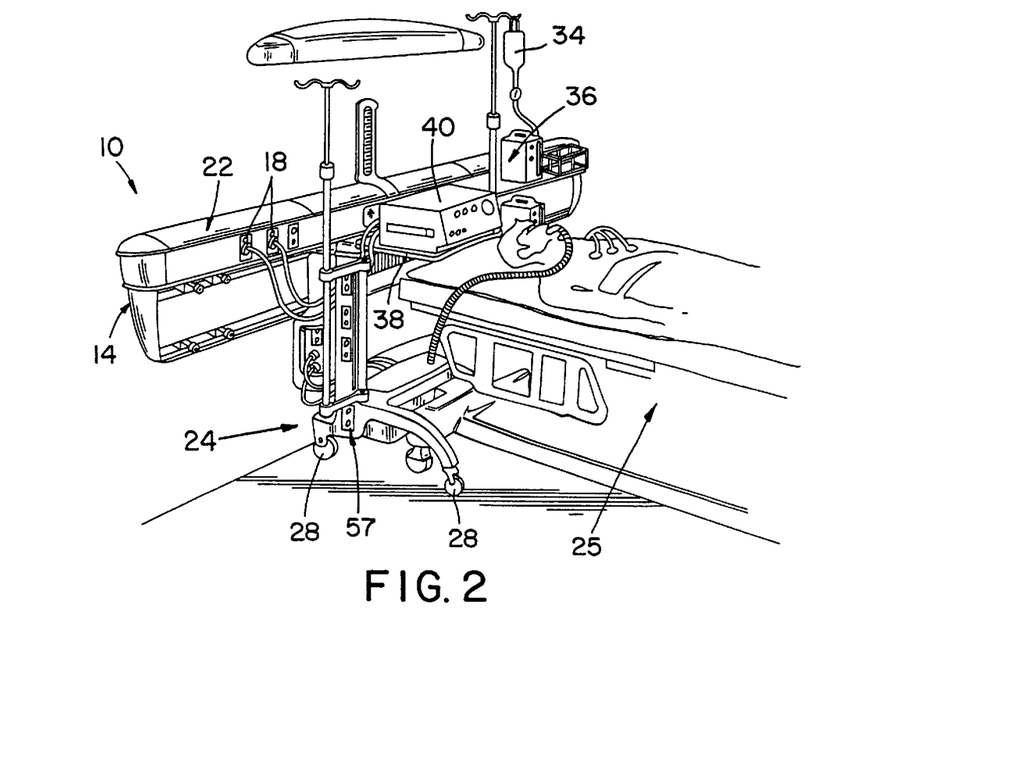
FIG. 2 is a perspective view illustrating the care cart docked or nested with the headwall and with a hospital bed positioned in the room adjacent the care cart to provide critical care services to a patient.
Figures 4, 5:
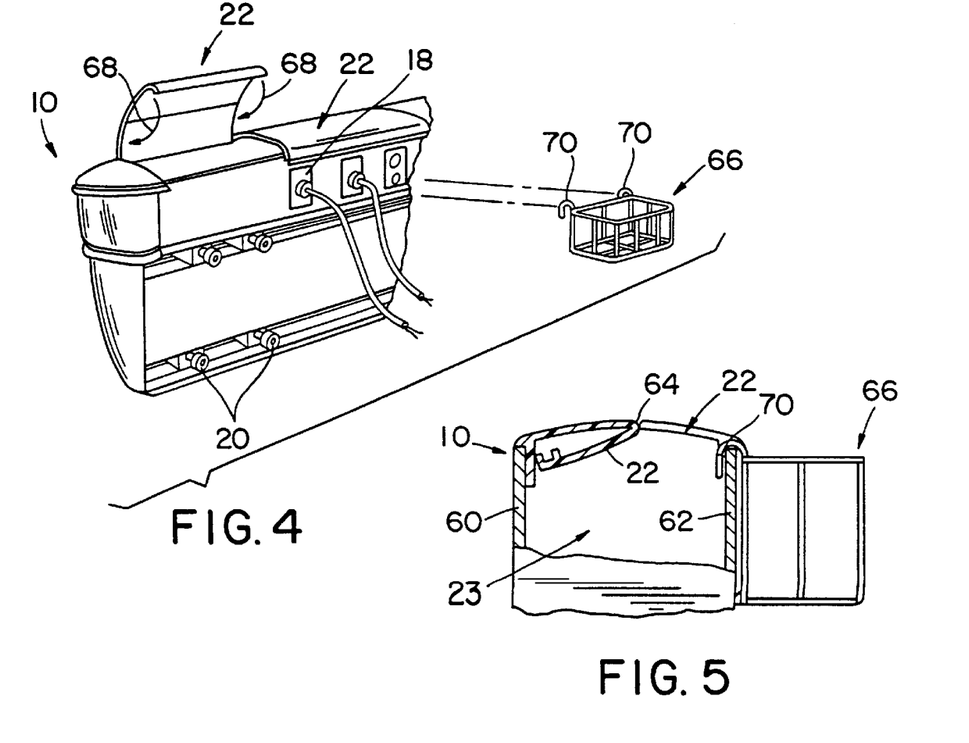
FIG. 4 is a partial perspective view of the headwall illustrating a foldable top or concealment cover which can be folded out of the way to provide access to an track for hanging an accessory item on a raceway of the headwall.
FIG. 5 is a sectional view taken through the headwall with an accessory item hanging on the track of the raceway.

Referring now to the drawings, FIGS. 1 and 2 illustrate the system and structural components of the present invention for providing a hospital room capable of upgrading services quickly and inexpensively. As illustrated in FIG. 1, a headwall 10 is mounted on a wall 12 of a hospital room. The headwall 10 includes an elongated body section 14 and a bed locator section 16. The headwall 10 includes outlets 18 for electrical power and outlets 20 for oxygen, air, and vacuum. Preferably, outlets 20 are movable gas outlets. The headwall 10 also includes a foldable concealment cover 22 configured to hide an internal raceway 23 as best illustrated in FIGS. 4 and 5. The headwall 10 can be used by itself in the room to provide for general care and support and for med-surg patients, for example.

Figure 3:
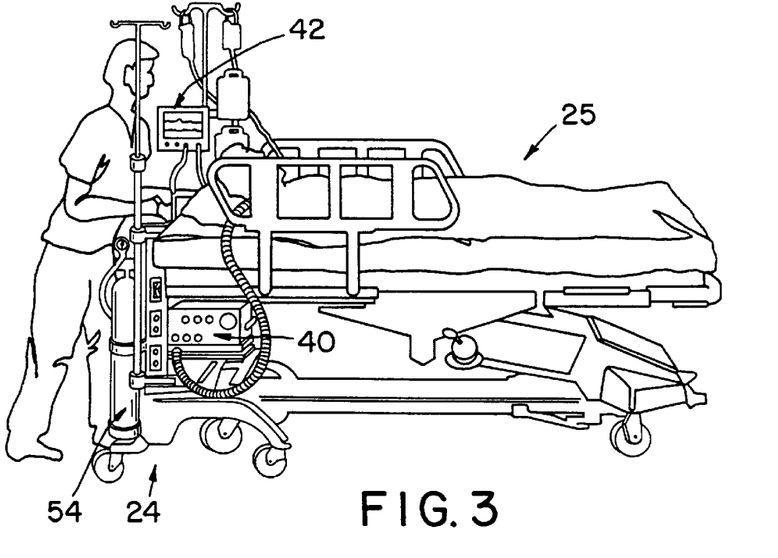
FIG. 3 is a side view illustrating transport of the patient on the bed docked with the mobile care cart.

When it is desired to upgrade the hospital room into a critical care room, a care cart 24 is moved into the room. The care cart 24 includes a base 26 having casters 28. The rear casters 28 are lockable by separate brakes 29. A pair of pivoting IV poles 30 are mounted on the base 26. The poles 30 include hooks 32 for hanging IV bags 34. IV pumps 36 may also be mounted on the poles 30. Care cart 24 also includes an equipment support shelf 38 for supporting a full end ventilator 40 or other critical care equipment. Ventilator 40 may be secured to the shelf 38 by latching brackets (not shown). A transport monitor 42 can also be mounted to care cart 24 during transport as illustrated in FIG. 3.

The support shelf 38 is movable from an elevated, in-room position illustrated in FIGS. 1 and 2 to a lowered transport position illustrated in FIG. 3 as discussed in detail below. The movable equipment shelf 38 therefore facilitates transport of the ventilator 40 with the care cart 24 during movement of the critical care patient.

The mobile care cart 24 further includes an air hose 44, an oxygen hose 46, a battery power cord 48, and a standard power cord 50. It is understood that a single cord may be used if desired. Care cart 24 also includes a transport battery 52 to operate equipment during transport of the critical care patient. The battery 52 provides power for the ventilator 40 and other critical care equipment during transport. The IV pumps 36 and transport monitor 42 each typically have an internal power supply. The battery 52 is recharged when the care cart 24 is plugged into the wall outlets 18.

Figures 6, 7, 9:
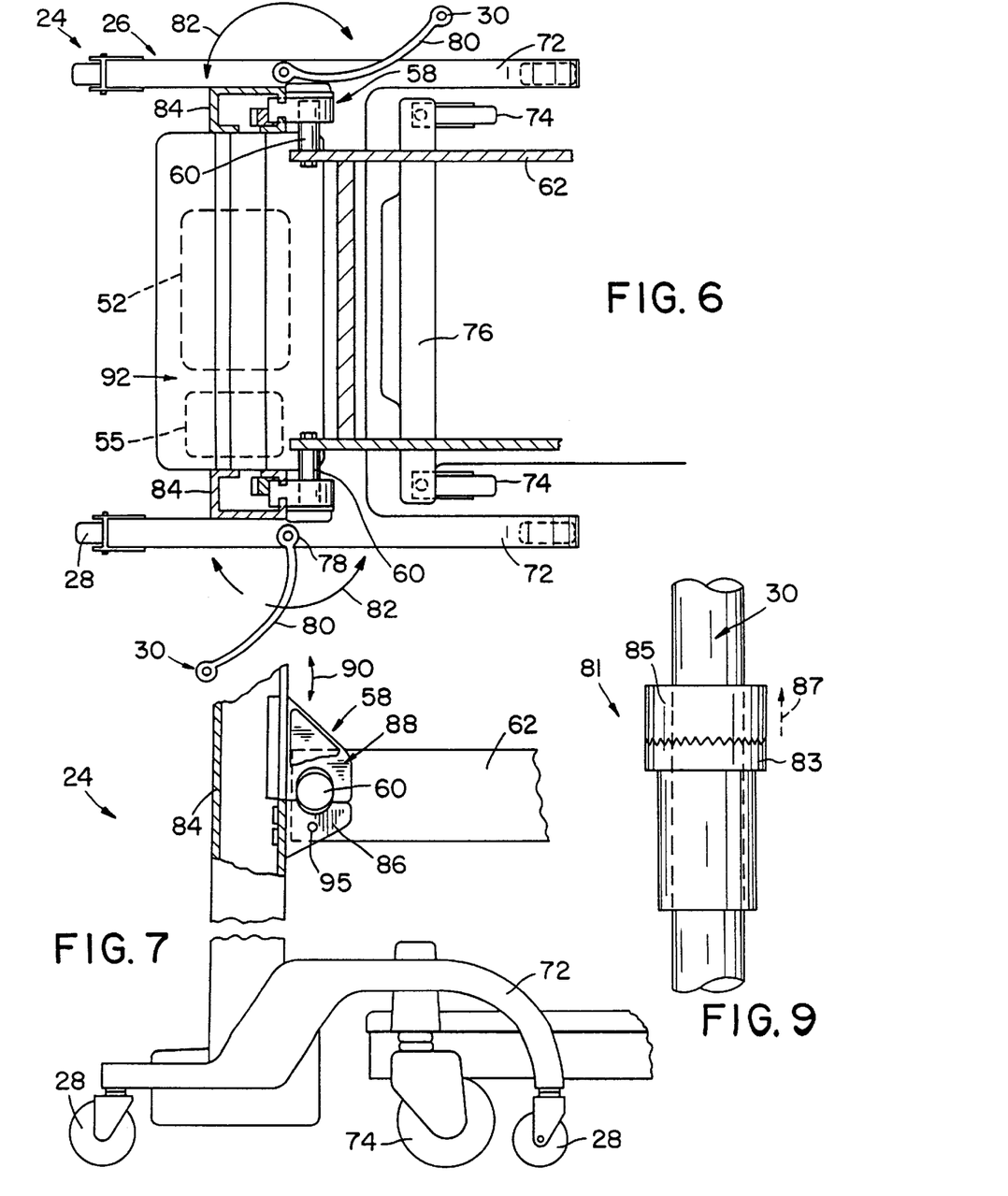
FIG. 6 is a sectional view taken through the mobile care cart when the mobile care cart is docked to the hospital bed.
FIG. 7 is a partial sectional view further illustrating coupling of the mobile care cart to the hospital bed.
FIG. 9 is an elevational view of a ratcheting detent mechanism located on pivoting IV poles coupled to the care cart.

FIG. 6 also illustrates a vacuum pump 55 for providing integral suction on the cart 24. A vacuum level adjustment controller, gauge, and connector are also included on the care cart 24 to provide suction on the cart 24 during transport.

Care cart 24 includes an upper series of electrical outlets 56 which are powered only when the care cart is plugged into the headwall outlet 18. Care cart 24 includes separate power outlets 57 which are automatically powered by the battery 52 when the care cart 24 is unplugged from outlets 18. Therefore, the equipment requiring power during transport must be plugged into the designated lower outlets 57 for an uninterrupted power supply from the battery 52.

In order to upgrade the hospital room to a critical care room, care cart 24 is moved into the position illustrated in FIG. 2. Power cords 48 and 50 are plugged into the outlets 18 of headwall 10. Air and oxygen lines 44 and 46 are connected to the gas outlets 20. In the position of FIG. 2, the battery 52 is recharged and air and oxygen tanks 54 are shut off to keep the tank supplies from being depleted. Also as illustrated in FIG. 2, the care cart 24 is configured to nest with the locator section 16 of headwall 10. Therefore, the hospital room can be upgraded to a critical care room without reconstruction.

The care cart 24 is also used to transport the critical care patient within the hospital. For example, the care cart 24 is coupled to the hospital bed 25 as discussed below. Using the care cart 24 to transport the patient provides seamless care for the patient during transport to the radiology department or other diagnostic testing facility within the hospital.

When it is desired to transport the critical care patient, oxygen and air tanks 54 are loaded on to the care cart 24 as illustrated in FIG. 3. Transport monitor 42 is also attached to the care cart 24. Prior to transport, valves on the oxygen and air tanks are manually opened to supply gas through the manifold to the ventilator 40. The gas lines 44 and 46 and power cords 48 and 50 of care cart 24 are then disconnected from headwall 10. Battery 52 on care cart 24 automatically switch on to support the ventilator 40 when the power cords 48 and 50 are disconnected.

For transport, the equipment shelf 38 is lowered to the transport position illustrated in FIG. 3. For visualization of equipment, such as a ventilator 40, the equipment shelf 38 supporting the equipment 40 can be rotated if desired. The transport position of the equipment shelf 38 allows the equipment, such as a ventilator 40 to be transported under the sleep surface frame of the bed and within existing dimensions of the bed 25. This allows the equipment to be transported with the bed and still fit within existing elevators in the hospital.

Next, the care cart 24 is coupled to the bed as illustrated in FIGS. 6 and 7. Latch mechanisms 58 on the care cart 24 are used to couple the care cart 24 to pins 60 attached to frame 62 of the bed 25. It is understood that the care cart 24 can be coupled to either a head end or foot end of the bed 25.

The IV lines and vent circuits do not need to be disconnected from the patient prior to transport. The IV pumps 36 and ventilator 40 also do not need to be handled. This method maintains seamless, uninterrupted functioning of the life support to the patient.

The bed 25 and the care cart 24 are then transported as a unit as illustrated in FIG. 3. A caregiver can use a push-handle 55 to guide the care cart 24 and bed 25. During transport, the IV pumps 36 and monitor 42 operates on their own internal batteries. The equipment without internal batteries operate on the battery 52 of care cart 24 through designated outlets 57. Battery 52 provides battery power for the transport procedure. The number of staff required to transport a critical care patient is reduced by using the care cart 24 of the present invention. Therefore, the impact on the staff remaining in the critical care unit is also reduced.

At the destination, the care cart 24 is coupled to medical gas and wall electrical outlets to prevent depleting of the on-board gas tank 54 supplies and battery 52. A cross over valve 180 allows the cart to be connected to the medical gas supply for a limited period of time with negligible leakage of gas from the tanks 54. The patient can then be transferred to a scanning table. The bed 25 can be removed from the care cart 24 and taken from the room. Therefore, the care cart 24 can remain adjacent the scanning table to continue to provide life support for the patient.

The original transport procedures are followed for the return trip to the room. Upon returning the patient to the room, the care cart 24 is plugged into the electrical outlets 18 and gas outlets 20 as discussed above. The care cart 24 is separated from the bed to permit the ventilator 40 on the shelf 38 to be moved to the elevated position of FIGS. 1 and 2. The equipment shelf 38 is then rotated and reoriented so that the displays 136 on the critical care equipment 40 are facing outwardly into the room. A care cart 24 is then moved adjacent the hospital bed 25 to the nested position of FIG. 2 to resume in-room critical care services. It is understood that the care cart 24 can be positioned in any orientation at the head end of bed 25.

Further details of the headwall 10 are illustrated in FIGS. 4 and 5. Headwall 10 includes an upper raceway 23 defined by a rear wall 60 and a front wall 62. The compartment cover 22 is preferably an integral piece including a hinged portion 64 which is preferably formed by a groove in the extruded material which forms cover 22. Cover 22 is initially placed over raceway 23 to provide an aesthetically pleasing appearance to the patient. When it is desired to couple any accessory item such as basket 66 to the headwall 10, a desired portion of the cover 22 is moved upwardly. Cover 22 can then be pivoted about hinge 64 in the direction of arrows 68 to the position illustrated in FIG. 5. Therefore, hooks 70 of the basket 66 can be positioned over a top end of front side wall 62. It is understood that many types of accessory equipment can be coupled to front wall 62 of headwall 10 in this manner. It is also understood that the cover 22 may be formed without hinge 64.

Further details of the care cart 24 are illustrated in FIGS. 6 and 7. Opposite legs 72 of base 26 are wide enough to pass beyond casters 74 of the hospital bed base 76. Some types of hospital beds have a removable headboard and bumper frame. Therefore, when the care cart 24 is in the docked position of FIGS. 6 and 7, the care cart only takes up about as much room as a conventional headboard due to the nesting of the care cart 24 with the hospital bed 25. Other types of hospital beds have retractable frames allowing shortening of the bed length.

The pivoting IV poles 30 pivotably coupled with base 26 at locations 78. Connecting arms 80 extend from the pivot connections 78 to the IV poles 30. The illustrated connecting arms 80 are curved as shown in FIG. 6. The curved arms 80 follow the curved shape of the care cart 24 when the arms 80 are pivoted inwardly during transport. The IV poles 30 can pivot as indicated by arrows 82 to adjust the position of the IV poles 30 during in-room use or during transport.

The IV poles 30 are preferably coupled to the care cart 24 by a ratcheting detent mechanism 81 illustrated in FIG. 9. A fixed sleeve 83 includes teeth which mate with teeth on a sleeve 85 coupled to IV poles 30. Gravity holds the teeth together to prevent rotation of the pole 30. Pole 30 can be rotated by lifting the pole upwardly in the direction of arrow 87 to disengage the teeth of sleeves 83 and 85.

Figure 8:
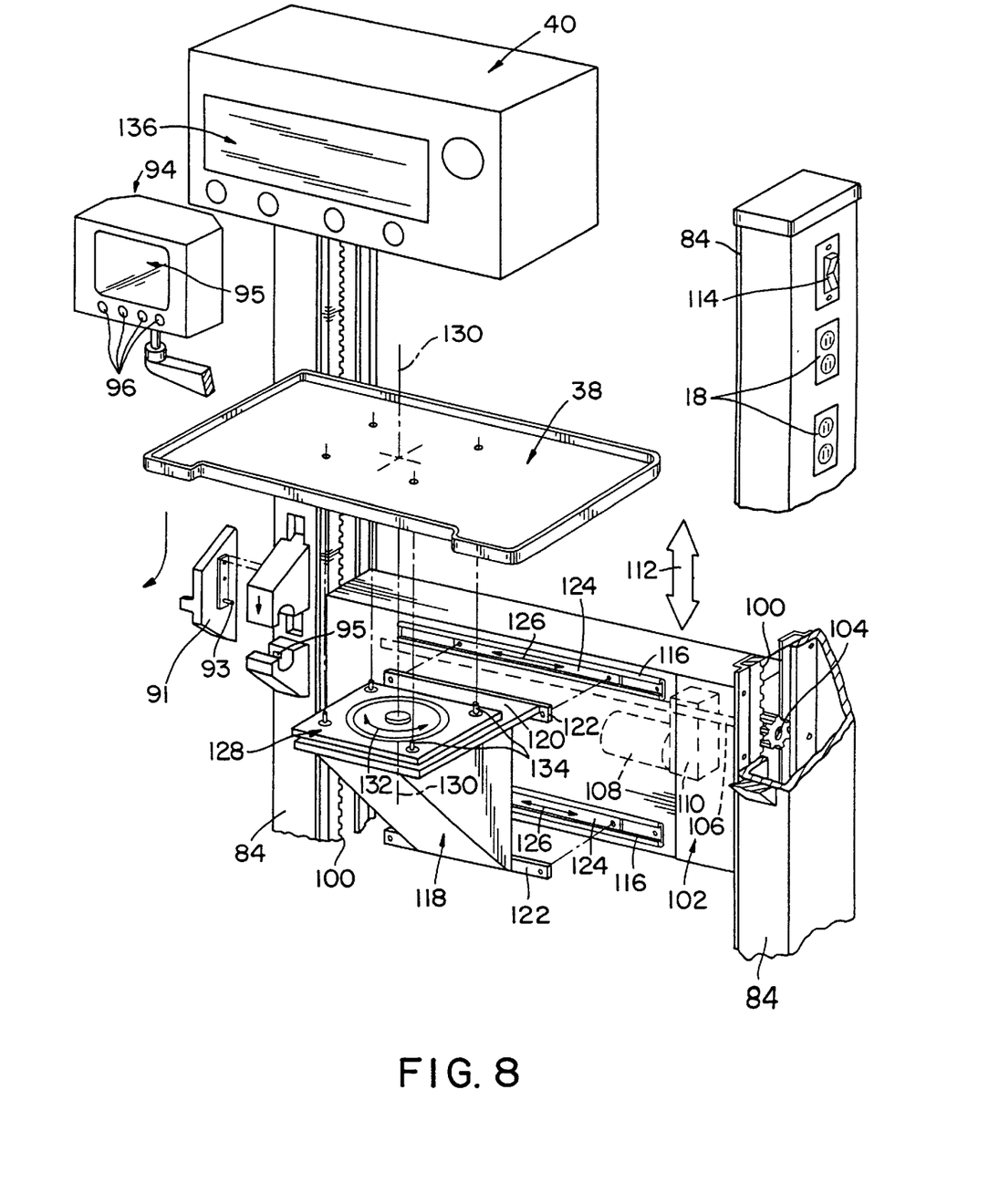
FIG. 8 is a perspective view illustrating the ventilator support equipment shelf of the mobile care cart.

The base 26 includes upwardly extending columns 84. Latching mechanisms 58 are coupled to the columns 84. The latching mechanisms 58 include a bottom section 86 which is rigidly coupled to the columns 84. A top latching section 88 is movable upwardly and downwardly in the direction of double headed arrow 90 of FIG. 7. An actuator section 91 is best illustrated in FIG. 8. When it is desired to couple the care cart 24 to the hospital bed 25, the upper latch sections 88 are moved to an upwardly extended position by actuator sections 91. The hospital bed height is then adjusted to match the height of latching mechanism 58. A height indicator (not shown) may be provided on the bed to provide a visual indication when the bed is at the proper elevation for mating with the care cart 24. After the height of the bed is adjusted, the care cart 24 is moved into the nested position over the end of the bed 25 so that the latching mechanisms 58 are aligned with the pin 60 connected to the frame 62 of bed 25. The upper latching sections 88 are then moved downwardly to a locked position as illustrated in FIG. 7. A pin 93 of actuator 91 enters as hole 95 formed in bottom latch section 86 to secure the latch mechanisms 58. Therefore, the care cart 24 and bed 25 can then be transported as a locked unit as illustrated in FIG. 3. In addition, the latching mechanism can be flexibly adjusted upwardly or downwardly on the column to accommodate various bed heights or pieces of equipment.

Before power cords 48 and 50 of the care cart 24 are disconnected from outlets 18, the caregiver must check to determine whether the on-board battery 52 on care cart 24 is properly charged. A display panel 94 shown in FIG. 8 is mounted on or near the top of the care cart 24. Display panel 94 can be flexibly positioned for viewing from several positions around the care cart 24. The panel 94 provides information on the charge status and condition of the on board battery 52 when the battery 52 is both plugged into the room and when discharging during transport. Care cart 24 includes a battery cover 92 for protection and concealment of the battery.

The display 94 illustratively includes two separate display sections. The first display section 95 provides a digital display of transport time and battery charge level. The second display section includes status indicator LEDs 96.

The first display section 95 displays the transport time during which the battery 52 is disconnected from the wall power supply. In addition, the display section 95 can be used to display the time remaining for the charge of battery 52 during a low battery state. Display section 95 also displays the charge level remaining for battery 52 on a percentage charge basis. The display can be either a digital numeric display, a bar graph or other indicator.

The operating status is indicated by LED indicators 96, or a LCD or other display. An indicator 96 is only illuminated when a particular condition exists. Illustratively, the status conditions include lighting a green indicator when a battery charging condition exists. Lighting a yellow indicator when no input power is detected. Providing a flashing yellow indicator when no ground is present. Providing a yellow indicator when no battery is present or when battery replacement is needed. Providing a red indicator when no output power is detected or if an overload condition is detected. An audible alarm can also be provided, if desired.

Further details of the care cart 24 are illustrated in FIG. 8. The supports 84 are formed to include an internal rack 100 having a plurality of teeth. A movable support 102 is coupled to supports 84. A gear 104 cooperates with each of the racks 100. A shaft 106 extends between the gears 104. A motor 108 and gearbox 110 are used to rotate shaft 106 and to move the support 102 up and down in the direction of double headed arrow 112 to control the height of shelf 38. A control switch 114 adjacent a top end of one support 84 controls motor 108 to move the support upwardly and downwardly in the directions of double headed arrow 112.

Top and bottom tracks 116 are coupled to movable support 102. Tracks 116 extend in a direction normal to an axis of rotation 130 of shelf 38. A mounting unit 118 includes a top surface 120 and a pair of mounting brackets 122 which are configured to be coupled to slides 124 located within tracks 116. Therefore, the mounted unit 118 and equipment shelf 38 are movable laterally relative to the movable support 102 and the base 26 in the direction of double headed arrows 126.

A swivel mounting plate 128 is coupled to top surface 120 of mounting unit 118. Swivel plate 128 can rotate a central axis 130 is illustrated by double headed arrow 132. Equipment shelf 38 is rigidly coupled to swivel plate 128 by fasteners 134.

Equipment shelf 38 is therefore adjustable vertically in the direction of double headed arrow 112, laterally in the direction of double headed arrows 126, and rotationally in the direction of double headed arrow 132. Therefore, a caregiver can adjust the position of the equipment shelf 38 and ventilator 40 relative to the care cart 24 to provide the best possible visualization for the display and control panel 136 of ventilator 40.

Figure 10:
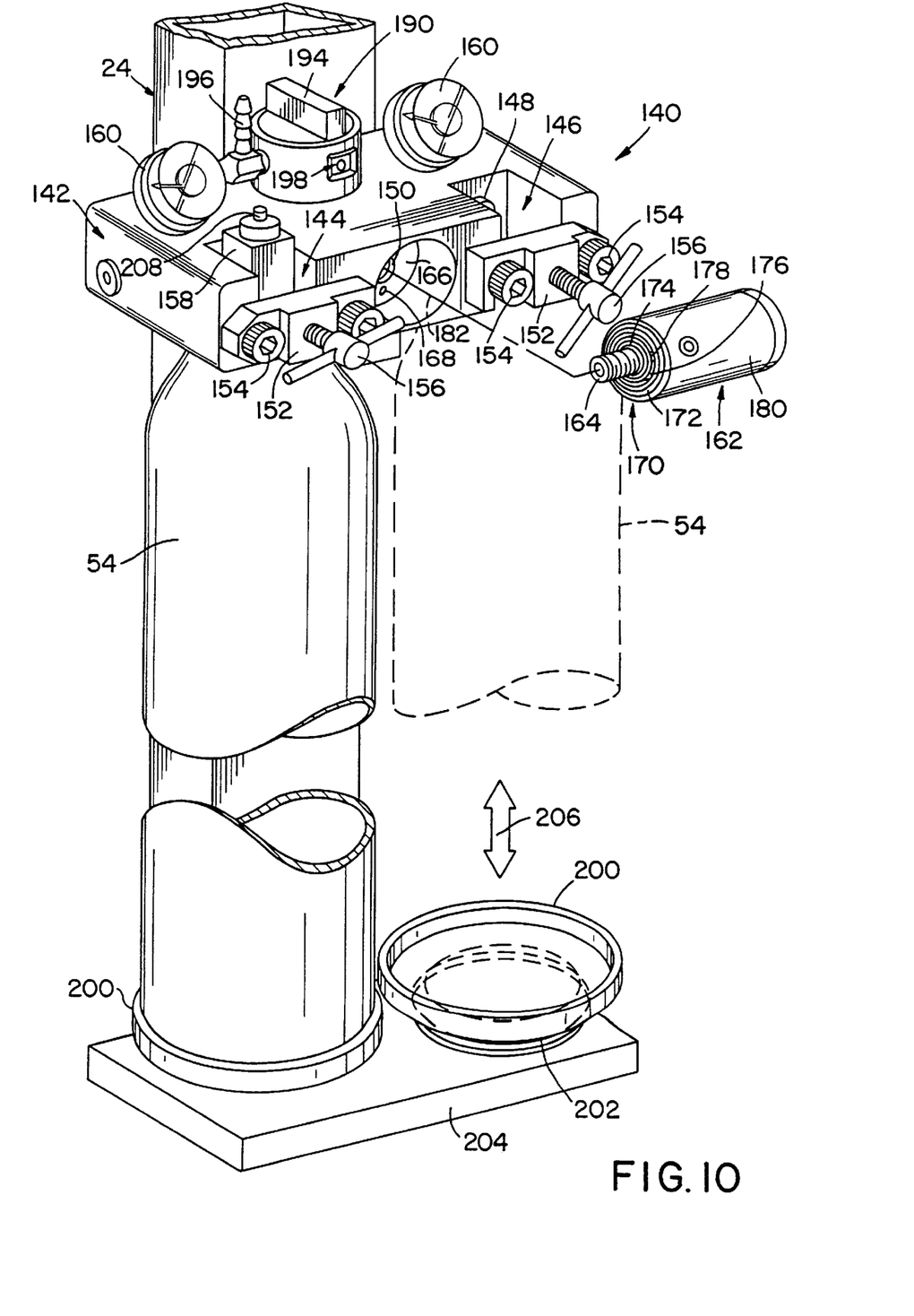
FIG. 10 is a perspective view of a manifold assembly for coupling oxygen or air tanks to the care cart and illustrating a pair of spring-loaded platforms for supporting gas tanks on the care cart.
Figure 11:
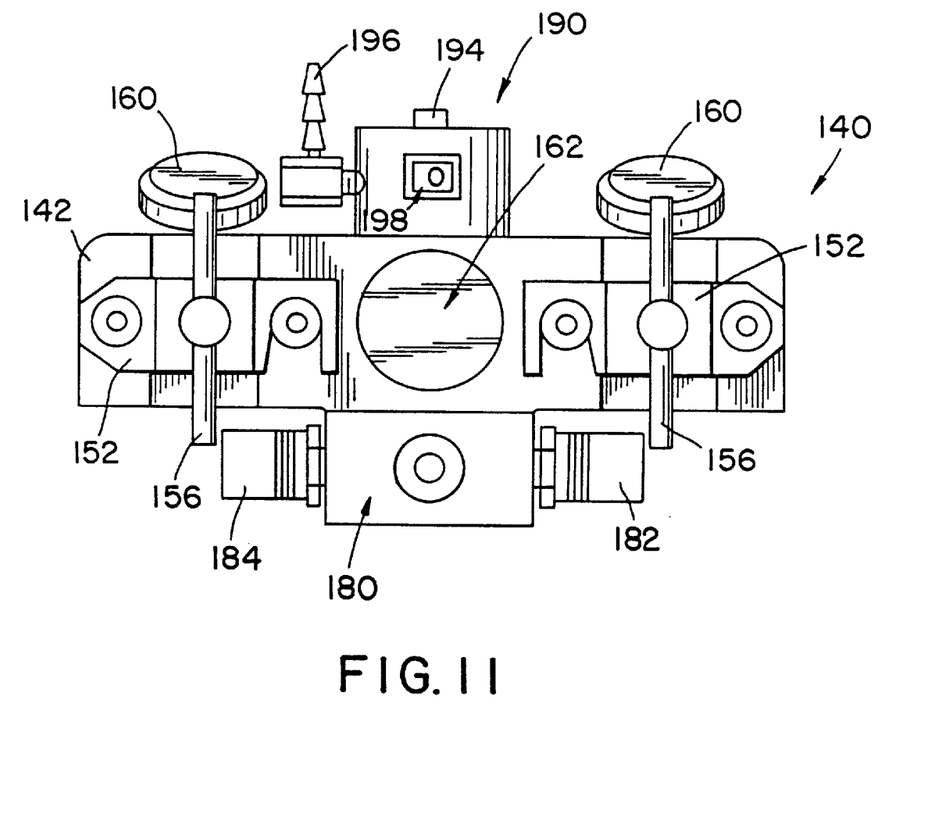
FIG. 11 is a front elevational view of the manifold of FIG. 10.

FIGS. 10 and 11 illustrate further details of a manifold assembly 140. Manifold assembly 140 includes a manifold block 142 coupled to care cart 24. Manifold block 142 includes first and second recessed sections 144 and 146 for receiving two separate air or oxygen gas tanks 54. A gas inlet 148 is located in each of recessed sections 144 and 146. Therefore, two gas inlets 148 are provided so that both tanks 54 supply single gas outlet 150. Gas inlets 148 are formed by sized threads designed to receive specific gas connections.

Mounting plates 152 and fasteners 154 are used to secure the tanks 54 to the manifold block 142. Retainers 156 are threaded into mounting plates 152. Retainers 156 force valve stems 158 of the tanks 54 against inlets 148 to seal the outlets (not shown) of valve stems 158. The recessed portions 144 and 146 of manifold block 142 provide protection for valve stems 158 of tanks 54. Therefore, the improved manifold assembly 140 facilitates loading and securing of the tanks 54 to the care cart 24, while protecting the valve stems 158.

The improved manifold assembly also manages the flow of gases to the ventilator 40. Separate pressure gauges 160 are provided for each tank 54. A regulator 162 is provided to step down the pressure from the tanks 54 from about 2200 psi to about 50–55 psi. Providing two separate tanks 54 coupled to the same outlet 150 provides a back-up gas tank 54 and permits switch out of the tanks 54 without interrupting the supply of gas. It is understood that separate manifold assemblies 140 are provided on care cart 24 for both air and oxygen.

Figure 12:
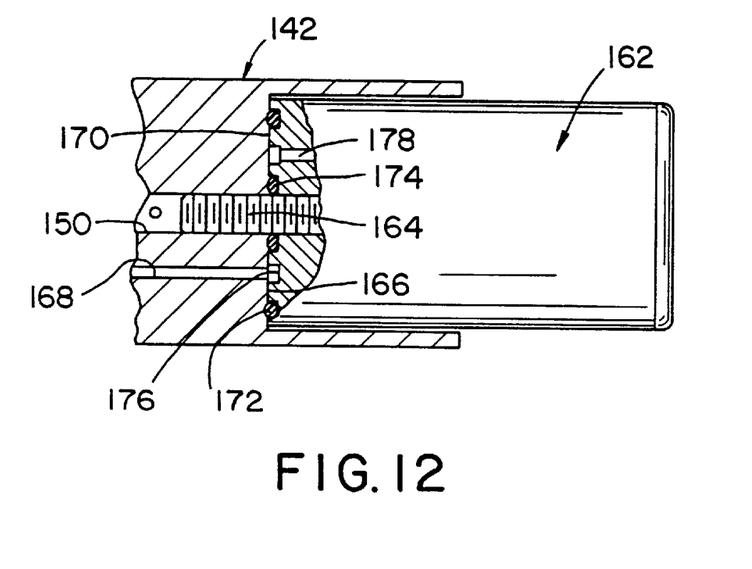
FIG. 12 is a sectional view of a manifold block and regulator when the regulator is installed into the manifold block as shown in FIG. 11.

Regulator 162 includes a threaded inlet 164 configured to be threaded into the threaded outlet aperture 150 from manifold block 142. Manifold block 142 includes a planar surface 166 formed to include the outlet aperture 150 and an inlet aperture 168 for receiving the regulated gas supply from regulator 162. The high pressure outlet aperture 150 and the reduced pressure inlet aperture 168 are located on the same planar surface 166. The inlet aperture 168 is spaced apart from the outlet aperture 150 by a selected distance.

Regulator 162 includes a regulator body including an end wall 170 having an outer annular seal 172, an inner annular seal 174 and an annular groove 176 formed between the inner and outer seals 172 and 174. Seals 172 and 174 are located within annular notches formed in end wall 170. An outlet aperture 178 of regulator 162 is formed in communication with the annular groove 176 as best shown in FIG. 12. The improved regulator 162 of the present invention facilitates alignment of the outlet 178 with the inlet aperture 168 on manifold block 142.

In prior art devices, an outlet is formed in a side wall 180 of regulator 162. One such prior art device is a model number RKX202-6092 regulator available from Flowtec Inc. located in Indianapolis, Ind. In these prior art devices, the outlet of the regulator must be rotated to a precise orientation to communicate with an inlet aperture formed in a side wall of a manifold block.

As shown in FIG. 12, the high pressure supply from tanks 54 passes through the outlet aperture 150 of manifold block 142 and into regulator 162 through threaded inlet 164. Outer seal 172 and inner seal 174 engage the planar surface 166 of manifold block 142 to provide a seal around the annular groove 176. The annular groove 176 is aligned with the inlet aperture 168 of manifold block 142. The outlet aperture 178 of regulator 162 is also aligned with the annular groove 176. Therefore, the gas from regulator 162 can flow from the outlet 178 to the inlet 168 regardless of the orientation of the regulator 162 relative to the manifold block 142. In other words, aperture 178 does not have to be aligned directly over the inlet aperture 168.

Seals 172 and 174 are located on opposite sides of gas inlet aperture 168. If the seals 172 and 174 extend far enough away from the end wall 170 of regulator 162 to define a gas flow path between the end wall 170 and the planar surface 166, the annular groove 176 may be omitted.

As illustrated in FIG. 11, a cross over valve 180 is coupled to manifold block 142. Cross over valve 180 receives a first input from inlet aperture 168 of manifold block 142. Cross over valve 180 includes a second inlet coupler 182 configured to be coupled to a gas supply wall outlet by a hose 44 or 46. An outlet connector 184 is also coupled to cross over valve 180. The outlet connector is configured to be coupled to the critical care equipment such as the ventilator 40 by a suitable hose connection.

Figure 13:
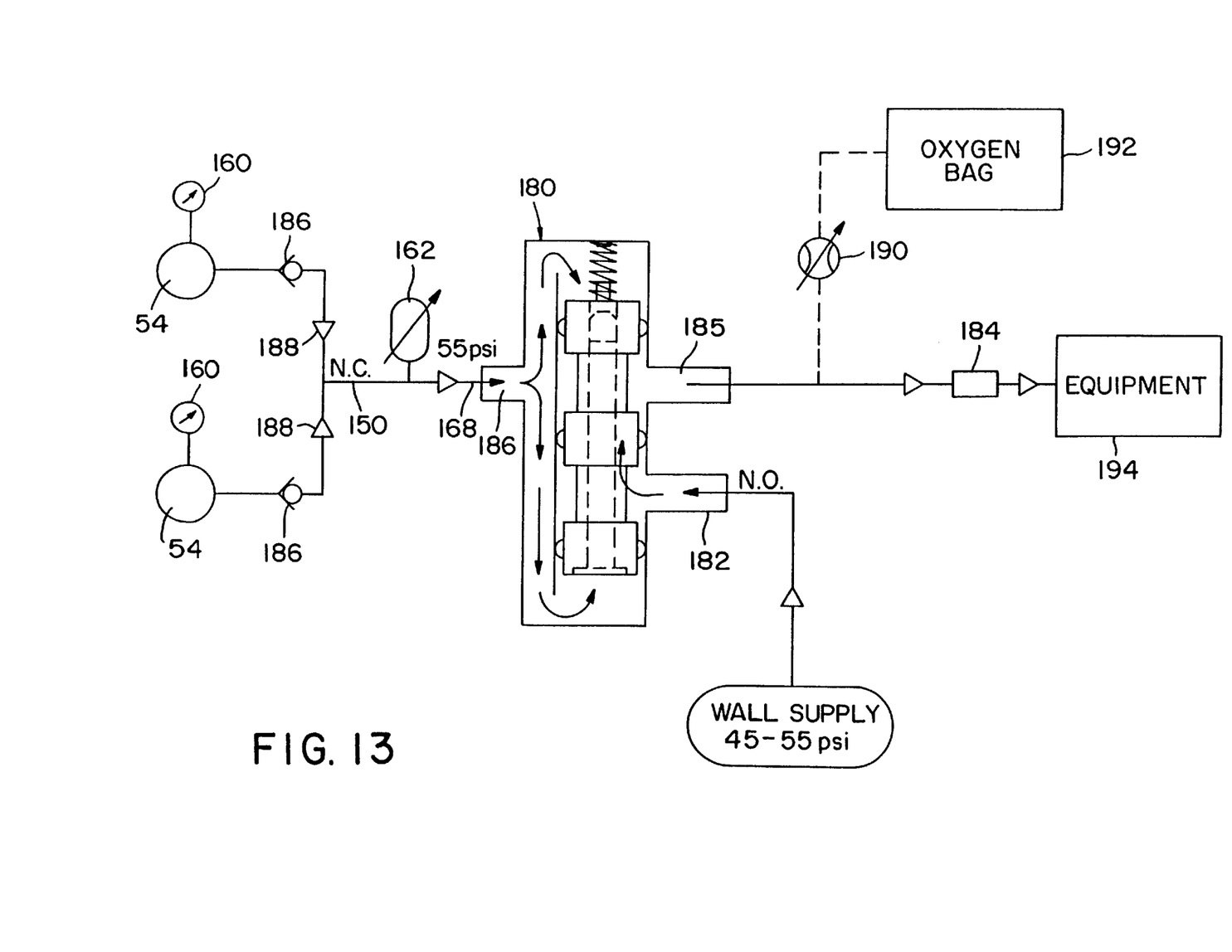
FIG. 13 is a schematic diagram of gas flow from first and second gas tanks and from a wall gas outlet through a crossover valve to the item of equipment on the care cart and to an auxiliary flow control valve.

A schematic diagram of the gas flow through the manifold assembly 140 is illustrated in FIG. 13. Check valves 186 are located within manifold block 142 and coupled to each tank 54 so that gas can flow only the direction of arrows 188. Both tanks 54 supply regulator 162 to reduce the pressure of tanks 54 from about 2200 psi to about 50–55 psi. Reduced pressure inlet aperture 168 supplies gas to a first inlet 186 of cross over valve 180. Illustratively, cross over valve 180 is a model number Y125 IN-VA1 valve available from Humphrey.

If the manifold assembly 140 is used for oxygen tanks, an adjustable flow control valve 190 is coupled to an outlet 185 of cross over valve 180. An outlet from the adjustable valve 190 is coupled to an oxygen bag 192 on the cart 24. An outlet connector 184 is coupled to critical care equipment 194, such as ventilator 40.

Details of the adjustable flow control valve 190 are illustrated in FIGS. 10 and 11. Valve 190 includes a rotatable actuator 194 for adjusting the gas flow rate through an outlet connector 196. A flow rate indicator 198 is also provided. Connector 196 is coupled to an oxygen bag 192 or other equipment.

FIG. 10 illustrates another feature of the present invention. A pair of tank support platforms 200 are provided for supporting tanks 54. A spring 202 is located beneath each platform 200. Springs 202 are supported by a rigid support 204. The spring-loaded platforms 200 facilitate adjustment of the position of tanks 54 on the cart 24. When stems 158 are installed onto tanks 54, the location of an outlet on stems 158 may vary. The spring loaded platforms 200 facilitate adjustment of the tanks 54 so that an outlet of stems 158 is aligned with the inlets 148 of manifold block 142. Therefore, the tanks 154 can be loaded onto spring-loaded platforms 200 and then adjusted in the direction of double-headed arrow 206 to align the outlet of stems 158 with the inlets 148 of the manifold block 142.

In operation, tanks 54 are loaded on to the care cart 24. When it is desired the transport the patient, an actuator (not shown) is used to open a valve 208 on tanks 54 to permit gas flow from the tanks into the manifold block 142. During transport, gas is automatically supplied from tanks 54 through the manifold block 142 and cross over valve 180 to the critical care equipment 194. Regulator 162 reduces high pressure from the tanks 54 to a working pressure of the critical care equipment 194. Separate pressure gauges 60 are provided for each tank 54 to provide visual inspection of the remaining capacity within the tanks 54. Check valves 186 prevent gas flow from one tank 54 to the other tank 54.

At the transport destination, the inlet 182 of cross over valve 180 is coupled to a wall source gas supply. Gas supply from the wall sources shuttles the cross over valve 180 to stop flow of gas from the tanks 54 to the equipment 194. Gas supply from the wall outlet is immediately directed to the critical care equipment 194. Disconnecting the wall supply from the cross over valve 180 automatically allows gas flow from the tanks 54 to the critical care equipment 194, provided that the tank valves 208 are open. The oxygen flow control valve 190 delivers oxygen flow to the oxygen bag 192 when the valve 180 receives a gas supply from either the wall gas source or the tanks 54. Once the cart 24 is returned to the hospital room and the cross over valve 180 is again connected to the wall gas supply, and the valves 208 of tanks 54 are closed to conserve gas within the tanks 54.

Although the invention has been described in detail with reference to a certain preferred embodiment, variations and modifications exist within the scope and spirit of the present invention as described and defined in the following claims.

What is claimed is:

1. An apparatus to permit upgrading of a hospital room from a general care room to a critical care room and to facilitate transport of a critical care patient on a hospital bed, the apparatus comprising:

a head wall mounted to a wall of the hospital room, the head wall including electrical outlets, gas supply outlets, and a bed locator section; and a mobile care cart including a base having casters, an equipment shelf coupled to the base for supporting an item of equipment, oxygen and air manifolds coupled to the cart, the manifolds each including at least one gas inlet configured to be coupled to a gas tank and an outlet, a gas supply line for coupling each manifold to the gas supply outlet of the head wall when the care cart is in the hospital room, a valve coupled to the manifold having a pressure responsive means for automatically shifting the supply of gases from the head wall outlet to the gas tank inlet to supply the equipment during transport, a battery coupled to the base, a power cord configured to be plugged into the electrical outlet in the head wall for recharging the battery and for powering the equipment when the mobile care cart is in the hospital room, the battery providing an uninterrupted power supply to the equipment when the power cord is unplugged for transport, the mobile care cart being configured to be moved into the hospital room and located adjacent the bed locator section of the head wall to upgrade the hospital room to a critical care room, the mobile care cart also including a latching mechanism for coupling the mobile care cart to the hospital bed to provide seamless care for the patient on the hospital bed during transport.

2. The apparatus of claim 1, wherein the mobile care cart includes a movable support coupled to the base, a drive mechanism coupled to the base and to the movable support to move the movable support from an elevated position to a downwardly extended transport position, the equipment shelf being rotatably coupled to the movable support to facilitate access to the equipment located on the equipment shelf in either the elevated position or the transport position.

3. The apparatus of claim 2, wherein the equipment shelf is located under an end of the hospital bed when the base is coupled to the hospital bed and the movable support is in its transport position.

4. The apparatus of claim 2, wherein the rotatable coupling of the equipment shelf is slidably coupled to the movable support to permit lateral movement of the equipment shelf relative to the movable support and the base in a direction normal to an axis of rotation of the equipment shelf.

5. The apparatus of claim 1, further comprising an indicator coupled to cart for indicating a condition of the battery.

6. The apparatus of claim 5, wherein the indicator includes a display panel.

7. The apparatus of claim 5, wherein the indicator includes an alarm for providing a signal indicative of the condition of the battery.

8. The apparatus of claim 1, further comprising at least one IV pole rotatably coupled to said base by a ratcheting detent mechanism.

9. The apparatus of claim 1, wherein the manifolds each include a manifold block having first and second recessed sections configured to receive a valve stem of the gas tanks, and first and second inlets configured to be coupled to the gas tanks, and a single outlet so that both the first and second gas tanks supply gas to the single outlet of the manifold.

10. The apparatus of claim 1, further comprising a vacuum pump coupled to the base of the care cart to provide suction on the care cart during transport.

11. A mobile care cart apparatus comprising:
a movable base;
a latching mechanism on the base for coupling the base to a hospital bed during transport of the hospital bed;
a movable support coupled to the base;
patient equipment to be carried on the moveable support;
a drive mechanism coupled to the base and to the movable support to move the movable support from an elevated position to a downwardly extended, transport position; and
an equipment shelf with a generally horizontal disposed support surface rotatably coupled about a vertical axis to the movable support, the equipment shelf being rotatable relative to the base about the vertical axis to facilitate carrying and access to said patient equipment located on the generally horizontally disposed equipment shelf support surface.

12. The apparatus of claim 11, wherein the equipment shelf is configured to be located under an end of the hospital bed when the base is coupled to the hospital bed and the movable support is in its transport position.

13. The apparatus of claim 11, wherein the rotatable coupling of the equipment shelf is slidably coupled to the movable support to permit lateral movement of the equipment shelf relative to the support and the base in a direction normal to an axis of rotation of the equipment shelf.

14. The apparatus of claim 11, further comprising an electrical outlet coupled to the base for powering the item of equipment, a battery coupled to the base, a power cord configured to be plugged into an electrical outlet for recharging the battery and for powering the items of equipment when the mobile care cart is in a room, the battery providing an uninterrupted power supply to the items of equipment when the power cord is unplugged for transport.

15. The apparatus of claim 14, further comprising an indicator coupled to said base for indicating the condition of the battery.

16. The apparatus of claim 15, wherein the indicator includes a visual display.

17. The apparatus of claim 15, wherein the indicator includes an alarm for providing a signal indicative of the condition of the battery.

18. The apparatus of claim 11, further comprising at least one IV pole pivotably coupled to said base.

19. The apparatus of claim 11, wherein the base includes at least one upwardly extending support arm, a rack coupled to the support arm, and a gear coupled to the movable support and configured to engage the rack to move the movable support between the elevated position and the transport position.

20. The apparatus of claim 19, further comprising a rotatable rod coupled to the gear, and a motor for rotating the rod and the gear to move the movable support.

21. The apparatus of claim 11, wherein the movable support includes at least one track mounted transverse to an axis of rotation of the equipment shelf, and a mounting unit slidably coupled to the track for supporting the rotatable coupling of the equipment shelf.

22. The apparatus of claim 21, further comprising a swivel plate coupled to the mounting unit, the equipment shelf being coupled to the swivel plate.

23. The apparatus of claim 11, wherein the latching mechanism includes a bottom latch section rigidly coupled to the base and a top latch section movably coupled to the base, the top and bottom latch sections being configured to engage a pin coupled to the hospital bed.

24. A mobile care cart apparatus comprising a movable base, a manifold assembly coupled to the base, the manifold assembly including a manifold block having a gas inlet configured to be coupled to a gas tank located on the mobile care cart and a gas outlet, and an automatic cross over valve having a first input coupled to the gas outlet of the manifold, a second input configured to be coupled to a wall outlet gas supply by a gas supply hose, and an outlet, the outlet of the cross over valve being configured to be coupled to an item of equipment located on the care cart by a gas supply line, the cross over valve having a pressure responsive means configured to supply gas to the cross over valve outlet from the gas tank automatically when the wall outlet gas supply is disconnected from the gas supply hose and to supply gas to the crossover valve outlet from the wall outlet gas supply automatically when the wall outlet gas supply is connected to the gas supply hose.

25. The apparatus of claim 24, wherein the manifold block includes first and second gas inlets coupled to the gas outlet, the first and second inlets being configured to be coupled to first and second gas tanks, respectively, for supplying gas to the outlet of the manifold from both of the first and second gas tanks.

26. The apparatus of claim 25, wherein the manifold block includes first and second recessed portions configured to receive a valve stem of the first and second gas tanks, respectively, and first and second latching brackets for securing the first and second gas tanks to the manifold block so that the manifold block protects the valve stems of the first and second gas tanks.

27. The apparatus of claim 25, further comprising first and second pressure gauges coupled to the first and second inlets to provide an indication of the pressure within the first and second tanks, respectively.

28. The apparatus of claim 24, further comprising a pressure regulator coupled between the gas inlet and the gas outlet of the manifold.

29. The apparatus of claim 28, wherein the manifold includes a gas outlet aperture formed in a planar surface and a gas inlet aperture formed in the planar surface spaced apart from the gas outlet aperture by a first distance, and the pressure regulator includes a regulator body for reducing gas pressure, the body including an end wall having a regulator inlet configured to be coupled to the gas outlet aperture, a first annular seal located a second distance from the regulator inlet, the second distance being less than the first distance, a second annular seal located a third distance from the regulator inlet, the third distance being greater than the first distance, and a regulator outlet formed in the end wall between the first and second seals, the first and second seals being configured to engage the planar surface on opposite sides of the gas inlet aperture on opposite sides of the gas inlet aperture so that gas from the regulator outlet flows into the gas inlet aperture formed in the planar surface.

30. The apparatus of claim 29, wherein the end wall of the body is formed to include an annular groove surrounding the regulator inlet, the annular groove being spaced apart from the regulator inlet by the first distance so that the annular groove is aligned with the gas inlet aperture formed in the planar surface when the regulator inlet is coupled to the gas outlet aperture, the regulator outlet being formed in communication with the annular groove.

31. The apparatus of claim 24, further comprising a spring-loaded platform coupled to the base, the spring-loaded platform being configured to support a gas tank on the base.

32. The apparatus of claim 24, further comprising an auxiliary gas flow control valve coupled to the outlet of the cross over valve for providing auxiliary gas flow to another item of equipment on the care cart.

33. A mobile care cart apparatus configured to be located adjacent a hospital bed during transport of the hospital bed, the apparatus comprising:

a movable base;

a manifold assembly coupled to the base;

the manifold assembly including a manifold block having a gas inlet configured to be coupled to a gas tank located on the mobile care cart and a gas outlet configured to be coupled to a first item of equipment located on the care cart; and the manifold block including a recessed portion configured to receive a valve stem of the gas tank and a latching bracket across the recessed portion for securing the gas tank to the manifold block and protecting the valve stems of the gas tank.

34. A mobile care cart apparatus configured to be located adjacent a hospital bed during transport of the hospital bed, the apparatus comprising:

a movable base;

a movable support coupled to the base;

a drive mechanism coupled to the base and to the movable support to move the movable support from an elevated position to a downwardly extended position; and the drive mechanism including at least one rack coupled to the base, a gear on the movable support and engaging the rack and a motor on the movable support rotating the gear to move the movable support.

35. A mobile care cart apparatus according to claim 34, including a pair of spaced racks coupled to the base, a pair of gears on the movable support and engaging the racks and the motor rotates the gears to move the movable support.

36. A mobile care cart apparatus configured to be located adjacent a hospital bed during transport of the hospital bed, the apparatus comprising:

a movable base;

a manifold assembly coupled to the base;

the manifold assembly including a manifold block having a gas inlet configured to be coupled to a gas tank located on the mobile care cart, a gas outlet configured to be coupled to a first item of equipment located on the care cart, a regulator inlet in a planar surface of the manifold block and connected to the gas inlet and a regulator outlet in the planar surface spaced from the regulator inlet and connected to the gas outlet; and a regulator mounted to the manifold block at the planar surface and including an inlet and an outlet on a common side of the regulator and having the same spacing as and communicating with the regulator inlet and outlet of the manifold block.

37. A mobile care cart apparatus according to claim 36, wherein one of the inlet and outlet of the regulator is annular and encompass the other.

* * * * *